(12) United States Patent
Abdou

(10) Patent No.: US 7,704,271 B2
(45) Date of Patent: Apr. 27, 2010

(54) DEVICES AND METHODS FOR INTER-VERTEBRAL ORTHOPEDIC DEVICE PLACEMENT

(76) Inventor: M. Samy Abdou, 7790 Doug Hill, San Diego, CA (US) 92127

( * ) Notice: Subject to any disclaimer, the term of this patent is extended or adjusted under 35 U.S.C. 154(b) by 247 days.

(21) Appl. No.: 11/613,074

(22) Filed: Dec. 19, 2006

(65) Prior Publication Data

US 2007/0167948 A1 Jul. 19, 2007

Related U.S. Application Data

(60) Provisional application No. 60/751,772, filed on Dec. 19, 2005.

(51) Int. Cl.
*A61B 17/70* (2006.01)
(52) U.S. Cl. .................. 606/266; 606/246; 606/264; 606/270; 606/272; 606/279
(58) Field of Classification Search .................. 606/246, 606/257, 259, 264–279; 411/380, 537
See application file for complete search history.

(56) References Cited

U.S. PATENT DOCUMENTS

| | | | |
|---|---|---|---|
| 4,309,777 A | | 1/1982 | Patil |
| 4,887,595 A * | | 12/1989 | Heinig et al. ............... 606/254 |
| 5,733,284 A * | | 3/1998 | Martin ........................ 606/248 |
| 6,083,224 A | | 7/2000 | Gertzbein et al. |
| 6,241,730 B1 | | 6/2001 | Alby |
| 6,645,207 B2 * | | 11/2003 | Dixon et al. ................ 606/261 |
| 6,682,530 B2 | | 1/2004 | Dixon et al. |
| 6,802,844 B2 * | | 10/2004 | Ferree ........................ 606/258 |
| 6,884,241 B2 | | 4/2005 | Bertranou et al. |
| 2003/0125742 A1 | | 7/2003 | Yuan et al. |
| 2004/0133207 A1 | | 7/2004 | Abdou |
| 2004/0158247 A1 | | 8/2004 | Sitiso et al. |
| 2004/0204713 A1 | | 10/2004 | Abdou |
| 2005/0004573 A1 | | 1/2005 | Abdou |
| 2005/0131406 A1* | | 6/2005 | Reiley et al. .................. 606/61 |
| 2005/0177163 A1 | | 8/2005 | Abdou |
| 2005/0177164 A1 | | 8/2005 | Walters et al. |

(Continued)

FOREIGN PATENT DOCUMENTS

WO WO 2004/032726 4/2004

(Continued)

*Primary Examiner*—Eduardo C Robert
*Assistant Examiner*—Steven J Cotroneo
(74) *Attorney, Agent, or Firm*—Fred C. Hernandez; Mintz, Levin, Cohn, Ferris, Glovsky and Popeo, P.C.

(57) ABSTRACT

Within a given spinal segment, the stable vertebral level is identified. Within the lower lumbar spine, that level is most commonly at the sacrum. A bone fastener is rigidly affixed to the stable spinal segment and an interconnecting member is rigidly affixed to the bone fastener so as to form a cantilever construct. Vertebral bodies that exhibit aberrant spinal motion and/or mal-alignment relative to the stable segment are then attached to the interconnecting member using non-rigid bone fastener(s). The motion profile of the dynamic fastener can be varied and may be selected to provide the desired vertebral motion characteristics. The interconnecting member may be rigid or it may be alternatively made rigid parallel to the direction of greatest instability and non-rigid in the other planes.

18 Claims, 9 Drawing Sheets

U.S. PATENT DOCUMENTS

| | | |
|---|---|---|
| 2005/0273120 A1 | 12/2005 | Abdou |
| 2005/0288669 A1 | 12/2005 | Abdou |
| 2005/0288670 A1 | 12/2005 | Panjabi et al. |
| 2006/0036240 A1* | 2/2006 | Colleran et al. .............. 606/61 |
| 2006/0052872 A1 | 3/2006 | Studer et al. |
| 2006/0074488 A1 | 4/2006 | Abdou |
| 2006/0149278 A1 | 7/2006 | Abdou |
| 2006/0161154 A1 | 7/2006 | McAfee |
| 2006/0217710 A1 | 9/2006 | Abdou |
| 2006/0217719 A1 | 9/2006 | Albert et al. |
| 2006/0229615 A1 | 10/2006 | Abdou |
| 2007/0093828 A1 | 4/2007 | Abdou |
| 2007/0093829 A1 | 4/2007 | Abdou |
| 2007/0106383 A1 | 5/2007 | Abdou |
| 2007/0123884 A1 | 5/2007 | Abdou |

FOREIGN PATENT DOCUMENTS

| | | |
|---|---|---|
| WO | WO 2004/062482 | 7/2004 |
| WO | WO 2004/084774 | 10/2004 |
| WO | WO 2004/093702 | 11/2004 |
| WO | WO 2005/122922 | 12/2005 |
| WO | WO 2006/041963 | 4/2006 |
| WO | WO 2006/089292 | 4/2006 |
| WO | WO 2006/058221 | 6/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

* cited by examiner

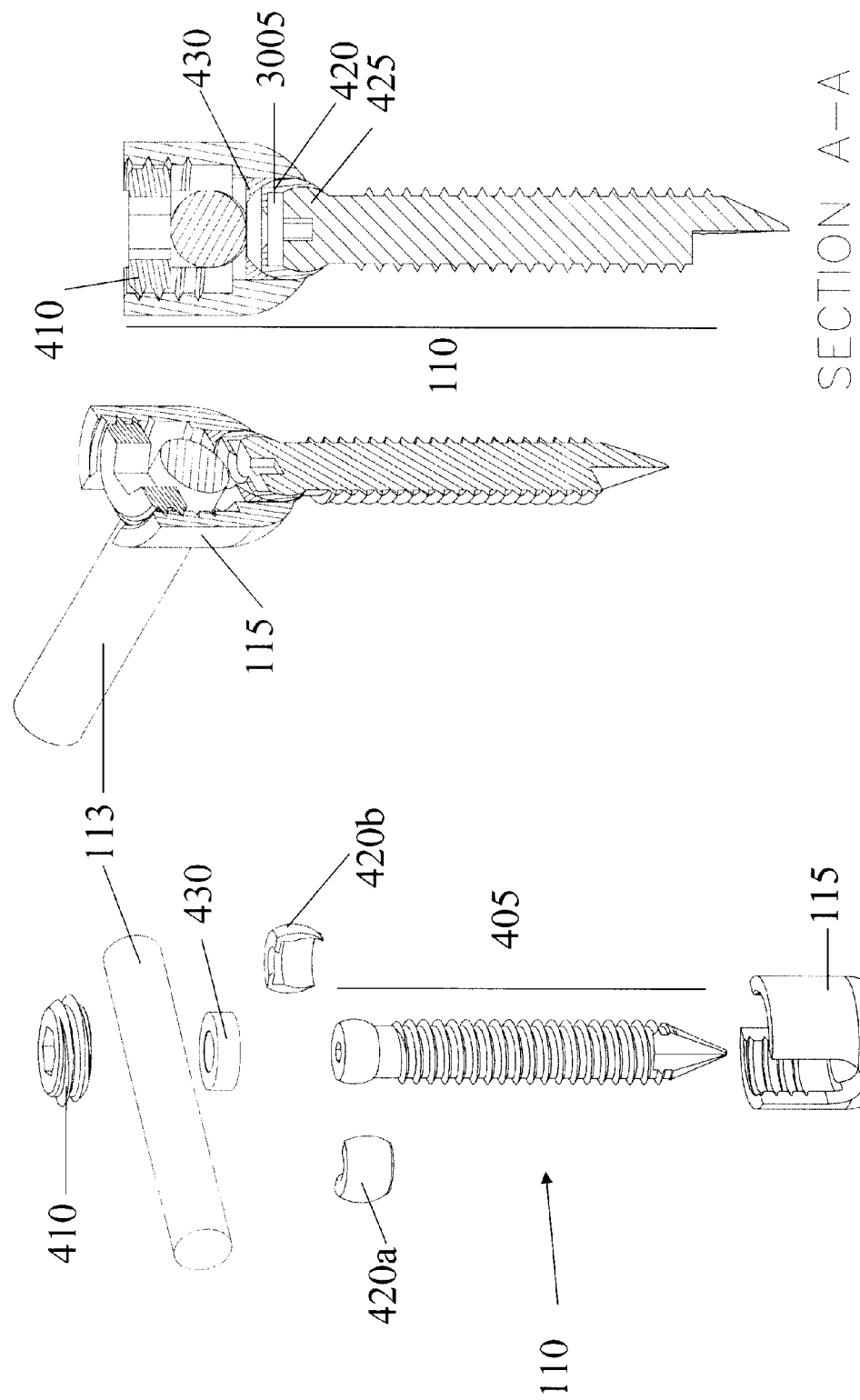

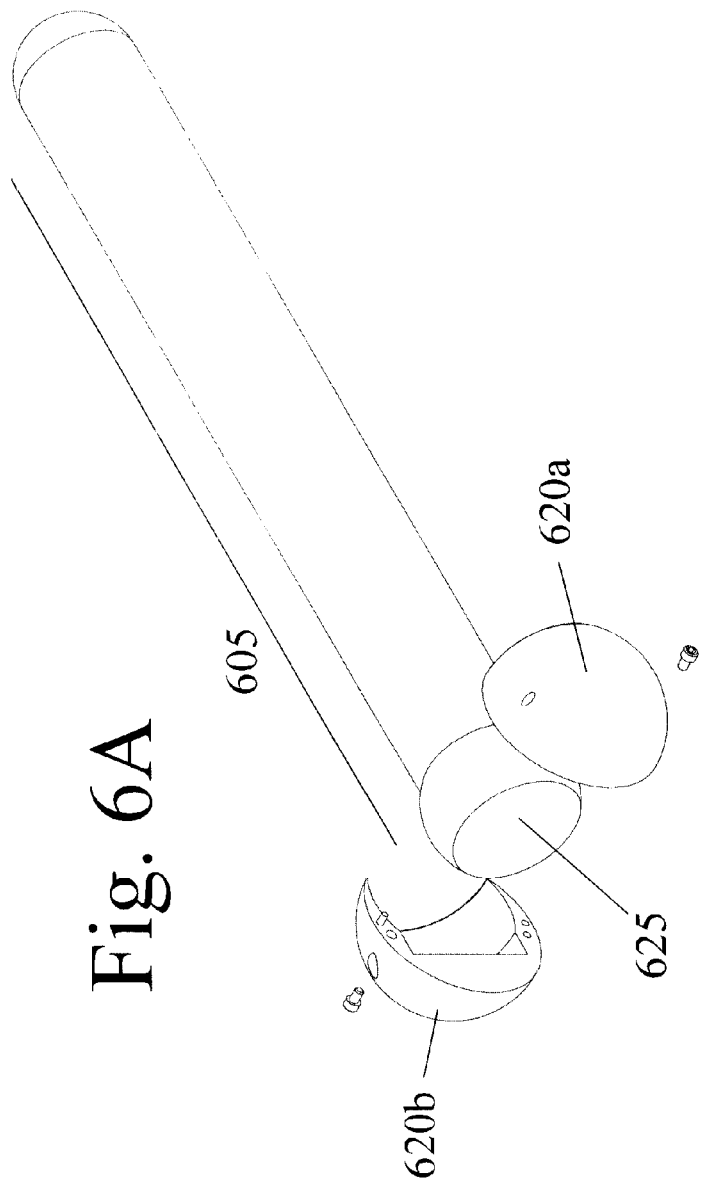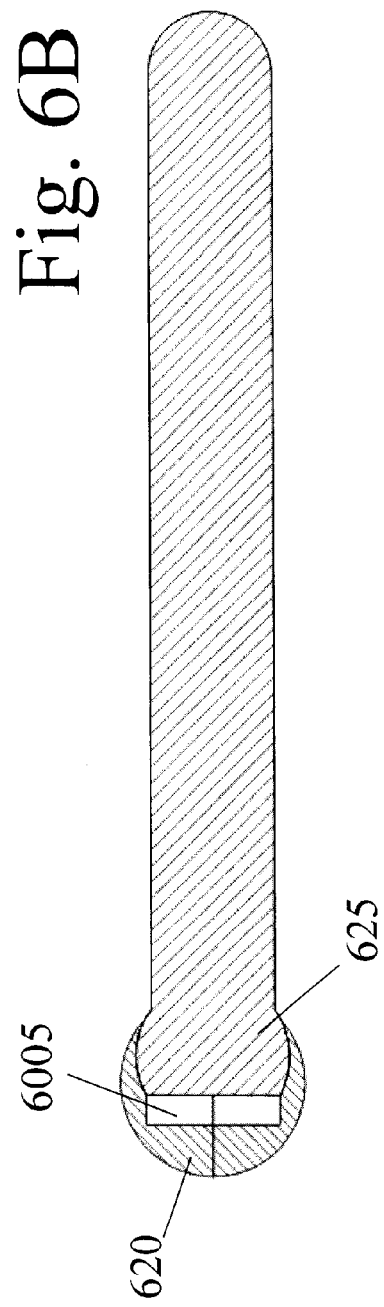

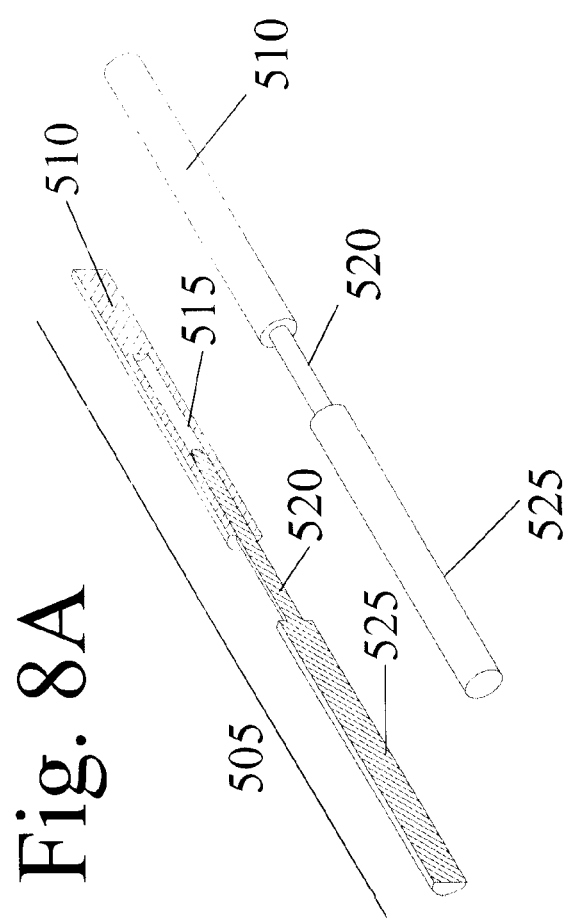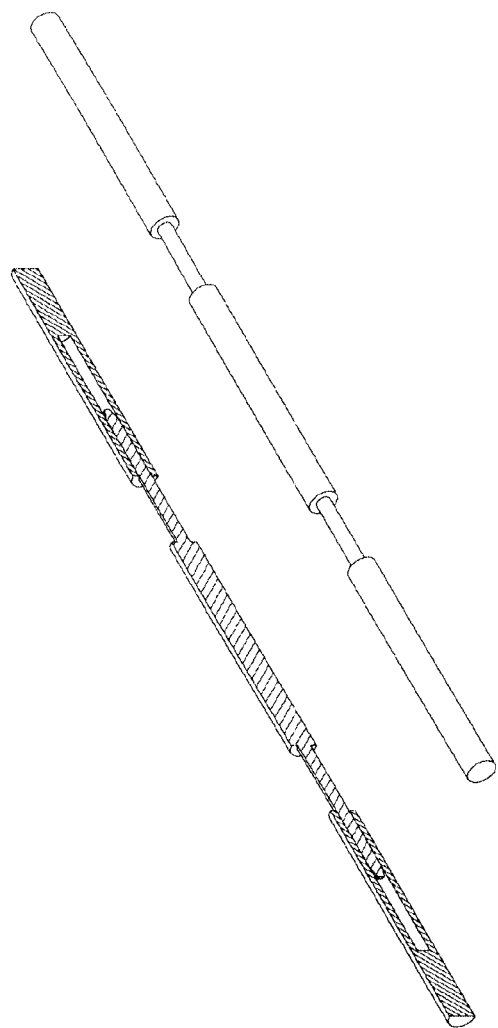

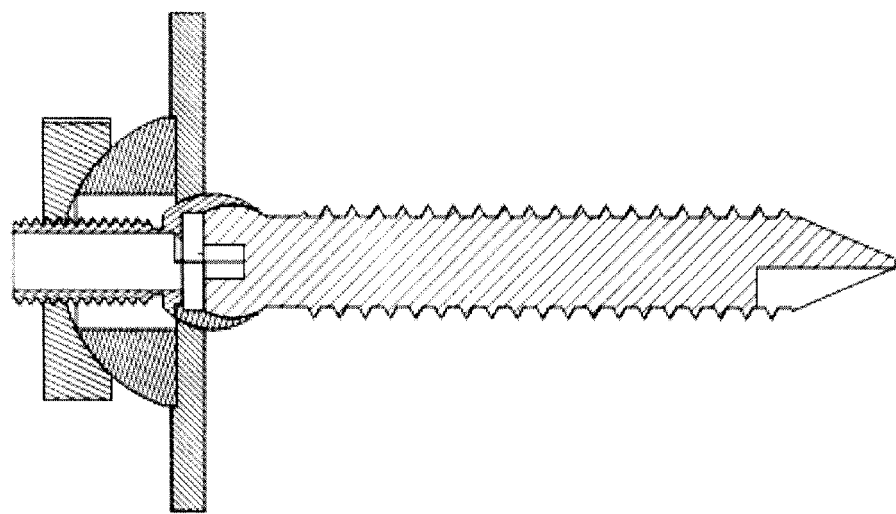
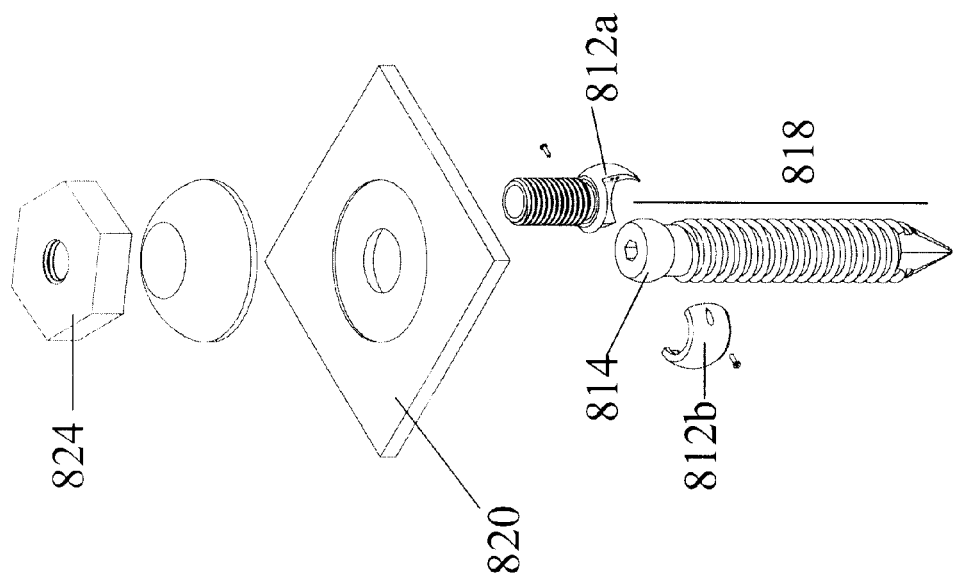

DEVICES AND METHODS FOR INTER-VERTEBRAL ORTHOPEDIC DEVICE PLACEMENT

REFERENCE TO PRIORITY DOCUMENT

This application claims priority of co-pending U.S. Provisional Patent Application Ser. No. 60/751,772, filed Dec. 19, 2005. Priority of the aforementioned filing date is hereby claimed and the disclosure of the Provisional Patent Application is hereby incorporated by reference in its entirety.

BACKGROUND

The disclosure relates to devices and methods for stabilization of the bony elements of the skeleton. The method and the devices permit adjustment and maintenance of the spatial relationship(s) between neighboring bones. Depending on the specifics of the design, the motion between skeletal segments may be increased, reduced, returned to the normal physiology state or modulated in any desired manner.

Spinal disease is a major health problem in the industrialized world and the surgical treatment of spinal pathology is an evolving discipline. Alteration in the anatomical alignment and physiologic motion that normally exists between adjacent spinal vertebrae can cause significant pain, weakness, deformity and disability. The traditional surgical treatment of abnormal vertebral motion has been the complete immobilization and bony fusion of the involved spinal segments. An extensive array of surgical techniques and implantable devices has been formulated to accomplish this goal.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The second procedure necessitates re-dissection through the prior, scarred operative field and carries significantly greater risk than the initial procedure while providing a reduced probability of pain relief. Further, extension of the fusion will increase the load on the motion segments that now lie at either end of the fusion construct and will accelerate the rate of degeneration at those levels. Thus, spinal fusion begets additional fusion surgery.

In view of the proceeding, there is a growing recognition that segmental spinal fusion and complete immobilization is an inadequate solution to abnormal spinal motion and vertebral mal-alignment. Correction of the abnormal movement and preservation of spinal mobility is a more intuitive and rational treatment option. It is appropriate to employ motion correction in the initial treatment plan and reserve complete immobilization and fusion for those patients with advanced motion abnormalities that can not be corrected.

Currently, a variety of spinal motion patterns are considered indications of advanced spinal instability. Patients with these motions patterns who develop pain are considered ineligible for treatment strategies that preserve spinal mobility. In particular, aberrant motion at levels of vertebral mal-alignment is considered an indication of disease that can not be corrected with current motion preservation methods. That is, surgeons believe that current motion correction techniques have a limited capacity to support the diseased spinal segments and those spinal segments with vertebral mal-aligned are too unstable to be effectively treated by these techniques.

Fusion and complete segmental immobilization remains the main surgical option for the surgical treatment of these patients.

The current limitations of motion preservation techniques needlessly relegate a large number of patients to fusion surgery and the numerous disadvantages of complete spinal immobilization. A method for the treatment of segments with aberrant motion and/or spinal mal-alignment without fusion is clearly needed. It would correct the abnormal motion and preserve mobility in a significant number of patients who must currently undergo spinal fusion.

SUMMARY

Spinal segments with abnormal motion and/or spinal mal-alignment can be successfully treated with devices that preserve mobility. Within a given spinal segment, the stable vertebral level is identified. Within the lower lumbar spine, that level is most commonly at the sacrum. A bone fastener is rigidly affixed to the stable spinal segment and an interconnecting member is rigidly affixed to the bone fastener so as to form a cantilever construct. Vertebral bodies that exhibit aberrant spinal motion and/or mal-alignment relative to the stable segment are then attached to the interconnecting member using non-rigid bone fastener(s). The motion profile of the dynamic fastener can be varied and may be selected to provide the desired vertebral motion characteristics.

The interconnecting member may be rigid or it may be alternatively made rigid parallel to the direction of greatest instability and non-rigid in the other planes. The latter embodiments provide additional degrees of freedom and motion characteristics.

In one aspect, there is disclosed a method of vertebral stabilization, comprising: rigidly affixing a first bone fastener to a first vertebral body and to an interconnecting member such that the interconnecting member is rigidly cantilevered from the first vertebral body; and affixing a second vertebral body to the interconnecting member such that the second vertebral body is attached to the interconnecting member in a manner that permits at least some movement between the second vertebral body and the first vertebral body.

In another aspect, there is disclosed a method of vertebral stabilization, comprising: rigidly affixing a first vertebral body to at least a portion of an interconnecting member such that the first vertebral body and the portion of the interconnecting member collectively form a rigid base; and affixing a second vertebral body to the rigid base in a manner that permits relative movement between the second vertebral body and the first vertebral body.

In another aspect, there is disclosed a method of vertebral stabilization, comprising: rigidly attaching an interconnecting member to a first vertebral body such that the interconnecting member is rigidly cantilevered relative to the first vertebral body; and attaching a second vertebral body to the interconnecting member such that the second vertebral body can move relative to the first vertebral body.

Other features and advantages will be apparent from the following description of various devices and methods, which illustrate, by way of example, the principles of these embodiments.

BRIEF DESCRIPTION OF THE DRAWINGS

FIGS. 1 and 2 show perspective views of the sacrum and the two lower most lumbar vertebrae.

FIG. 3 shows a cross sectional view of the sacrum and the two lower most lumbar vertebrae wherein the plane of section is along the long axis of the bone screws.

FIG. 5A shows an exploded view of an exemplary embodiment of a dynamic bone fastener or screw assembly.

FIG. 5B shows cross-sectional views of the dynamic bone screw assembly.

FIGS. 6A and 6B show a perspective exploded view and cross-sectional view of a dynamic rod device.

FIGS. 8A and 8B show embodiments of a rod that is adapted to provide movement along the long axis of the rod.

FIGS. 9A and 9B show an alternative dynamic screw assembly that may be used with a plate-based inter-connecting member.

DETAILED DESCRIPTION

Disclosed are devices and methods for providing segmental stabilization of bone segments while still preserving at least some relative motion between the segments. In an embodiment, one or more bone fasteners are rigidly attached to a bone segment at a stable level. An interconnecting member is then rigidly attached to the bone fastener(s) such that the interconnecting member extends outwardly from the fastener(s) and forms a cantilever construct. The bone fastener(s) and cantilevered interconnecting member provide a rigid, stable base to which adjacent bone segments can be movably attached. The adjacent bone segments are attached to the interconnecting member using a dynamic bone fastener(s) that is attached to the adjacent segment. The dynamic bone fastener permits at least some movement and, in this way, the adjacent segments can be dynamically attached to the stable vertebral segment.

The devices and methods are described herein in the context of bone segments comprised of the sacrum and the two lowermost lumbar vertebrae. Within the lumbar spine, these vertebral segments are the ones most commonly affected by degenerative disease and most often afflicted with abnormal alignment and pathologic motion. It should be appreciated that the devices and methods described herein are not limited to use within the lumbar spine and that they are equally suited for use with other skeletal segments.

Figure 2:
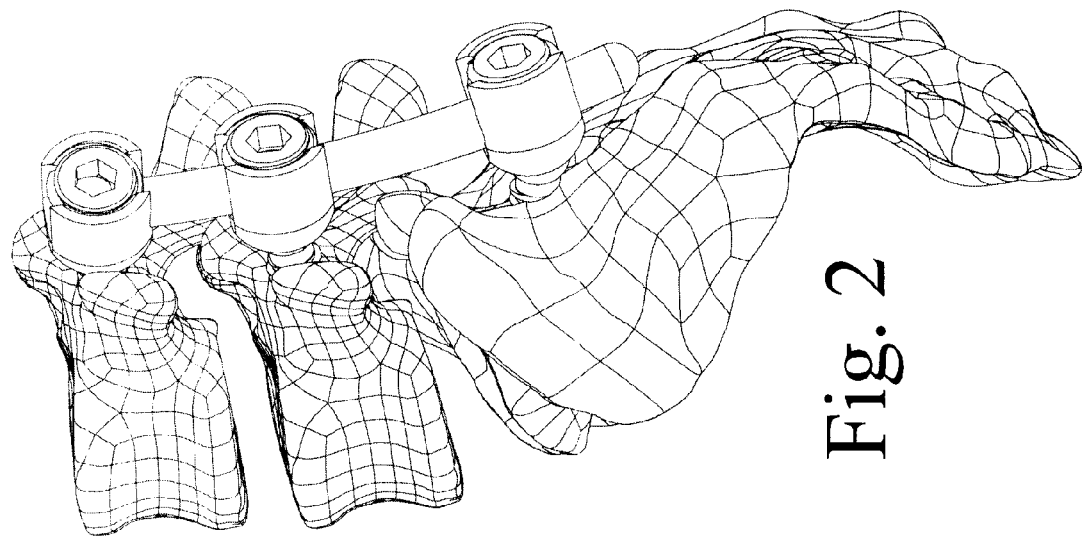
Figure 1:
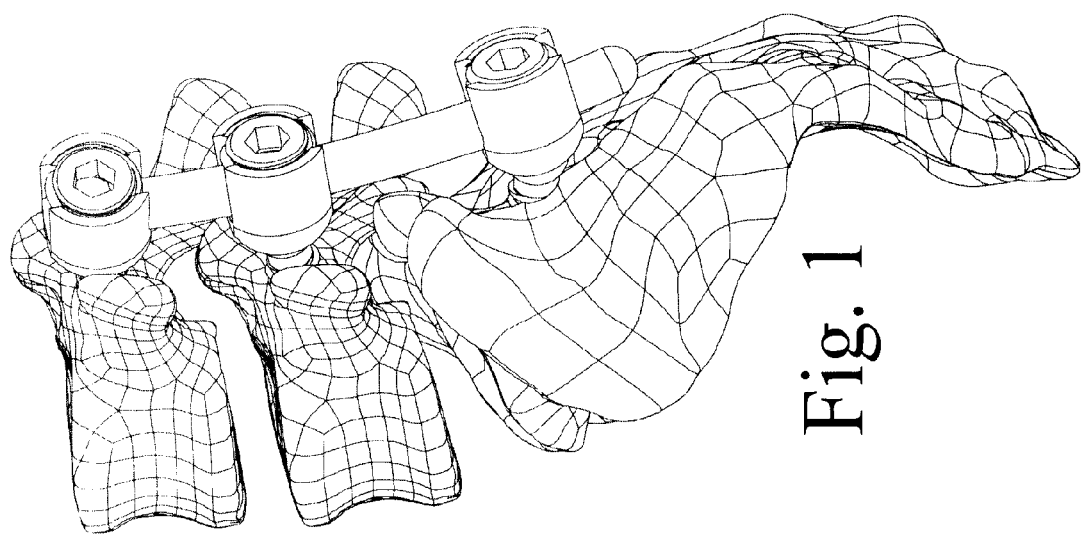
Figure 3:
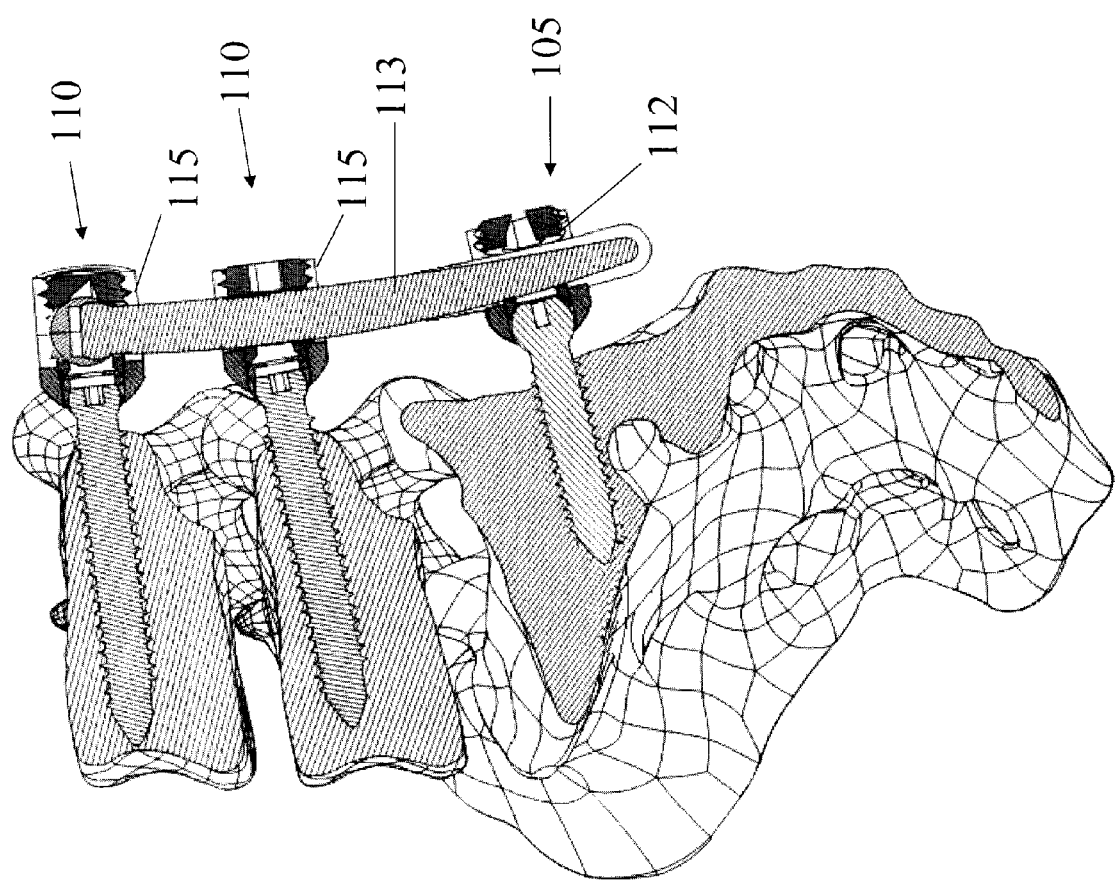

FIG. 1 shows a perspective view of the sacrum and the two lowermost lumbar vertebrae while FIG. 2 shows a schematic representation of the same view. In FIG. 3, a cross sectional illustration is shown wherein the plane of section is along the long axis of the bone screws. A bone screw assembly 105 is inserted into the sacrum such that a shank portion of a bone screw is rigidly positioned inside the sacrum. The bone screw assembly 105 includes a receiver 112 that rigidly attaches to a rod 113, as described in more detail below. The rod 113 extends outwardly from the bone screw assembly in cantilever fashion. In an embodiment, the bone screw assembly 105 is rigidly attached to the sacrum such that there is no movement between the bone screw assembly and the sacrum. In addition, the bone screw assembly 105 is rigidly attached to the rod 113 such that there is no movement between the bone screw assembly 105 and the rod 113. Thus, the rod 113 is immobilized relative to the sacrum. In this manner, the sacrum, bone screw assembly, and rod collectively form a rigid and stable base to which one or more additional bone segments can be attached.

With reference still to FIG. 3, bone screw assemblies 110 are inserted into each of the two lower most lumbar vertebrae such that shank portions of the screws are rigidly positioned inside the vertebrae such as within the pedicle segment of bone. Each of the bone screws assemblies 110 includes a receiver 115 that attaches to the rod 113 in a manner that permits at least some movement between the receiver 115 and the rod 113, as described in more detail below. In an embodiment, a screw of the assembly 115 rigidly attaches to the respective vertebrae, while a head of the screw is movably housed within a member 420 that is rigidly affixed to receiver 115. A bearing surface exists between the inner aspect of member 420 and the head of the bone screw. Thus, the vertebrae are movably attached to the rod via the bone screw assemblies 110. In this manner, the vertebrae are stabilized relative to the stable base (the rigid framework of the sacrum, bone screw assembly 105, and rod 1113) while still permitting at least some motion relative to the stable base. In other words, the rigid screw assembly 105 and rod 113 form a cantilever framework that is attached to the stable segment (sacrum). The dynamic screw assemblies 110 are then anchored into the vertebral bodies with abnormal alignment and/or motion and attached to the rigid rod. FIGS. 1, 2 and 3 show bone screw assemblies attached to a single side of the vertebral midline (unilateral placement) although it should be appreciated that screw insertion is preferably performed on both sides of the midline in actual practice. Further, while the illustrated embodiment shows a single bone screw assembly attached to each side of a vertebral body, more than one screw assembly may be used. Multiple screw attachment is particularly useful at the sacrum where the cantilevered interconnecting member may be affixed to the sacrum at multiple points. Multiple methods of sacral fixation are well known in the art and any of these may be utilized.

Figure 4B:
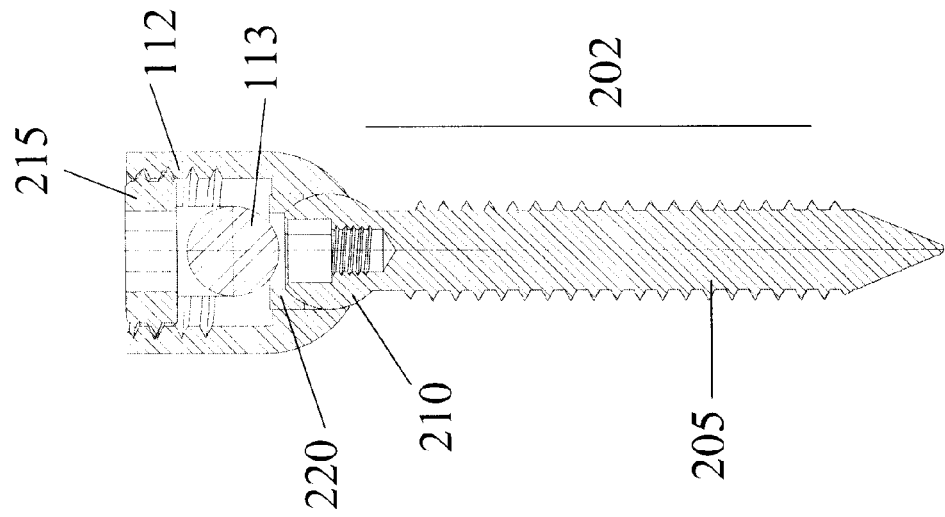
FIGS. 4A and 4B show perspective and cross-sectional views of an exemplary embodiment of a bone screw assembly that rigidly attaches to a rod.
Figure 4A:
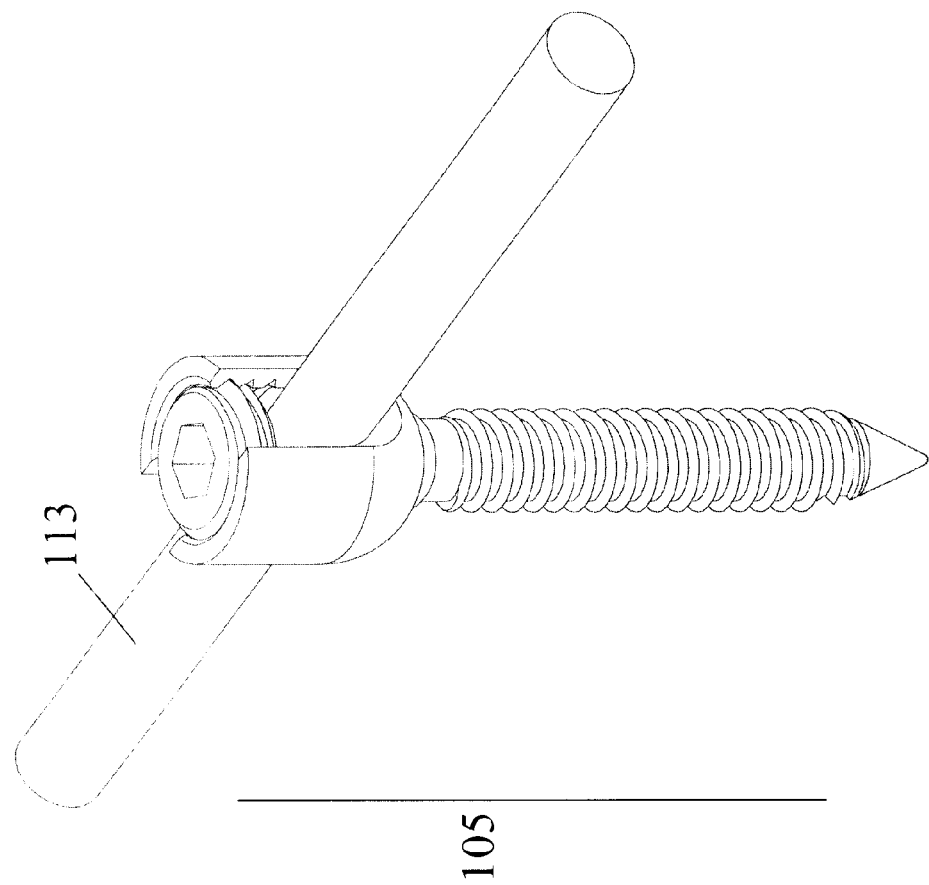

FIGS. 4A and 4B show perspective and cross-sectional views of an exemplary embodiment of the bone screw assembly that rigidly attaches to the rod 113. The bone screw assembly 105 includes a screw 202 with a shank 205 attached to a head 210. The head 210 sits within a seat in the rod receiver 112. A locking nut 215 can be tightened or advanced into the receiver 112 to compress the rod 113 onto the head 210 via a member 220 positioned between the head 210 and rod 113. When locking nut 215 is advanced, it forces the rod 113 against the member 220 which, in turn, compresses the screw head 210 against the inner aspect of receiver 112. When the locking nut 112 is fully advanced, the entire assembly becomes rigid and immobilizes the bone screw 202 relative to the receiver 112 and the rod 113.

It should be appreciated that the embodiment of the rigid bone screw shown in FIGS. 4A and 4B is exemplary and that other types of assemblies for rigidly attaching a bone screw to a rod can be used.

FIG. 5A shows an exploded view of the dynamic bone screw assembly 110 while FIG. 5B shows cross-sectional views of the screw assembly. As mentioned, the bone screw assembly 110 is dynamic in that it permits relative movement between the bone screw and the receiver 115. When the assembly is locked by the advancement of locking nut 410, the inner housing member 420 is immobilized relative to the receiver 115 and the contained rod 113 while the bone screw is rigidly attached to the vertebral body. However, the head of the screw can move in a ball and socket manner rotate within the inner housing member so as to permit continued movement between the bone screw and the interconnecting rod 113.

With reference to FIGS. 5A and 5B, the bone screw assembly 110 includes a receiver 115 and a bone screw 405, which couple to the rod 113. A locking nut 410 can be threaded into the receiver 115 to provide a downward force onto the rod 113 and immobilize the rod relative to the receiver 115 and the inner housing (420a and 420b). The bone screw 405 has a head 425 that can be positioned within inner housing members 420a and 420b. While not shown, half members 420a and 420b are joined to form the assembled inner housing member using threaded screws, ratchets, clips, adhesives, or any other well-known technique for segment assembly. A saddle 430 is positioned within the receiver 115 below the rod 113 and above the inner housing members 420 in the assembled device.

As shown in FIG. 5B, the head 425 of the screw 405 is positioned within the inner housing members 420, which collectively form a socket for the spherical head 425. The inner aspect of inner housing member 420 contains space 3005 that is positioned above the head 425. The saddle 430 is positioned directly above the inner housing 420 assembly and below the rod 113. In use, screw 405 is advanced into the underlying bone and affixed to it. Rod receiver 115 is freely movable relative to screw 115 based on the movement between the outer aspect of the inner housing member 420 and the complimentary spherical cut-out within the inner aspect of receiver 115. Rod 113 is positioned within the movable receiver 115 and the locking nut 410 is advanced toward the rod 113 to tightly press the rod 113 against the upper edge of the saddle 430. This causes the saddle 430 to press downward against the inner housing members 420 and forcefully seat it within receiver 115. In this way, rod 113, saddle 430, inner housing members 420 and receiver 115 are rigidly immobilized relative to one another. However, the head 425 of the bone screw 405 remains movable within the inner aspect of the inner housing members 420 to produces the dynamic properties of the assembly.

The space 3005 within the inner housing member 420 preferably contains a material or structure that resists movement of the head 425 of the bone screw 405 relative to the inner aspect of the inner housing members 420. Belleville washer(s), compression springs and the like can be placed within space 3005 to resist screw head movement and keep the upper surface of the screw head and upper surface of space 3005 in a parallel configuration. Alternatively, the material or structure within the space 3005 can be, for example, an elastic material(s), fluids, spring device(s), magnets or any other appropriate materials/devices that will resist movement of the head of bone screw relative to the inner aspect of the inner housing members. Clearly, the motion profile of the whole screw assembly will depend on the resistance characteristics of the material/device placed within space 3005. In this way, the motion of the dynamic fastener can be varied by changing the material in space 3005 and the fastener may be selected to provide the desired vertebral motion characteristics.

When the screw head is moved out of a predetermined neutral position within the inner housing members, the material/device in space 3005 will apply a force to the head of screw and resist any movement away from the neutral position. The assembly will return the screw and the attached bone to the neutral position once the deflecting force has dissipated. Further, since movement in the pre-locked configuration of the screw assembly occurs between the outer aspect of the inner housing 420 and receiver 115, the surgeon can freely adjust the orientation of the receiver 115 relative to the bone screw 405 before locking the assembly without influencing the assembly's neutral position or pre-loading the bone/screw interface.

It should be appreciated that the embodiment of the dynamic bone screw shown in FIGS. 5A and 5B is exemplary and that other types of assemblies for movably attaching a bone screw to a rod can be used.

Figure 7A:
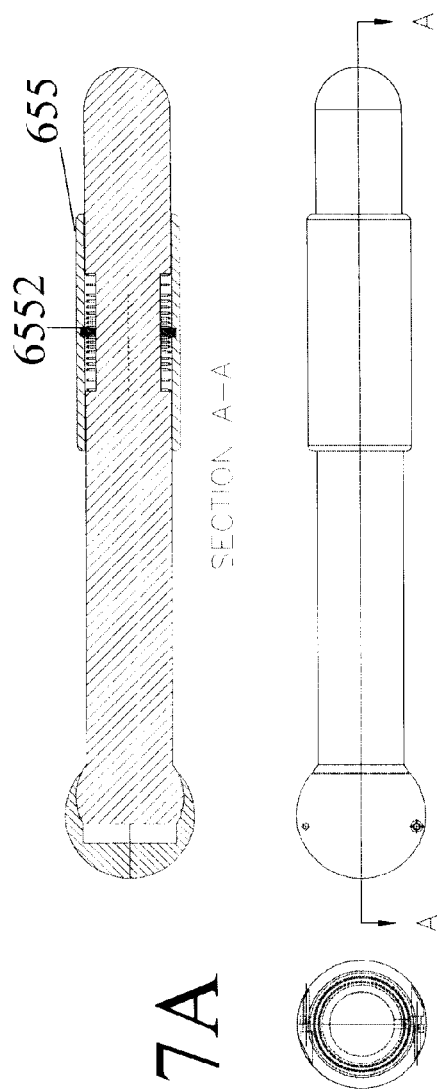
FIG. 7A shows the dynamic rod device equipped with a dynamic sleeve
Figure 7B:
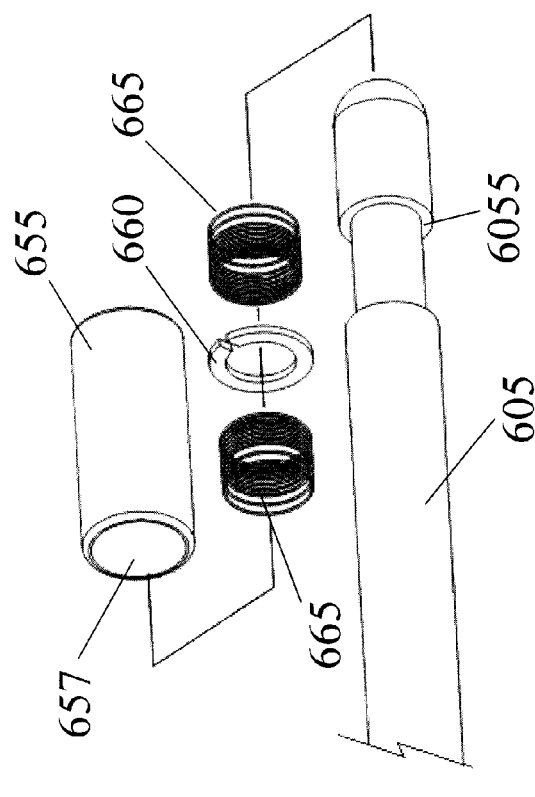
FIG. 7B shows an exploded view of one end of the dynamic rod device.

The interconnecting member may be of any applicable configuration and/or design. Commonly, the interconnecting member is rod-based, plate-based, loop-based or a combination of these elements. With reference to FIG. 3, the interconnecting member is a rod. The rod may be rigid or it may have dynamic features that confer additional motion characteristics onto to the assembled construct. The rod illustrated in FIG. 3 contains a dynamic terminus. FIGS. 6A and 6B show a perspective exploded view and cross-sectional view of the dynamic rod device, respectively. The dynamic feature is similar in design to the dynamic screw assembly 110 that is shown in FIG. 5. That is, the rod 605 has a head 625 that can be positioned within inner housing members 620a and 620b. Partial members 620a and 620b are joined to form the assembled inner housing member using threaded screws, but ratchets, clips, adhesives, or any other well-known technique for segment assembly may be alternatively used. The inner aspect of inner housing member 620 contains a space 6005 that is positioned above the head 625. The space 6005 within the inner housing member 620 preferably contains a material or structure that resists movement of the head 625 of the rod relative to the inner aspect of the inner housing members 620. With movement of head 625 away from the predetermined neutral position within the inner housing members 620, the material/device in space 6005 will apply a force to head 625 and resist any movement away from the neutral position. FIG. 7A shows a dynamic sleeve that has been added to the embodiment of FIG. 6 while FIG. 7B shows an exploded view of one end of the rod. Outer sleeve 655 has internal bore 657 that receives rod 605. Indentation 6552 is located on the inner wall of bore 657 and is configured to accept ring 660. Rod 605 has recess 6055. In assembly, each spring 665 is placed on either side of ring 660. The ring is retained within indentation 6552 of sleeve 655 and functions to limit the extent of travel and retain the device in assembled configuration.

Another embodiment of a dynamic feature is shown in FIGS. 8A and 8B. The rod is adapted to permit movement in the direction of the long axis (even If the axis is curvilinear). In FIG. 8A, the rod 505 includes a first rod segment 510 having an internal bore 515 that slidably receives a shaft portion 520 of a second rod segment 525 wherein the first rod segment 510 and second rod segment 525 are movable relative to one another. In FIG. 8B, the rod 505 can include more than two segments.

FIGS. 9A and 9B show an alternative dynamic screw assembly that may be used with a plate-based inter-connecting member. The assembly employs a housing member 812 with an internal socket feature that accepts the complimentary spherical head 814 of bone screw 818. As before, partial members 812a and 812b are joined to form the assembled housing member 812 using threaded screws, but ratchets, clips, adhesives, or any other well-known technique for segment assembly may be alternatively used. The inner aspect of housing member 812 contains space that is positioned above the head 814. The space within the housing member 812 preferably contains a material or structure that resists movement of the bone screw head 814 relative to the inner aspect of the housing member 812. The assembly permits the orientation of member 812 to be freely adjustable relative to plate interconnecting member 820 (partially shown) before the assembly is locked. After deployment of locking nut 824, plate 820 is rigidly immobilized relative to housing member 812. However, screw 818 will remain mobile within the inner aspect of housing 812 as previously described in the embodiments of FIGS. 5 and 6.

Figure 10:
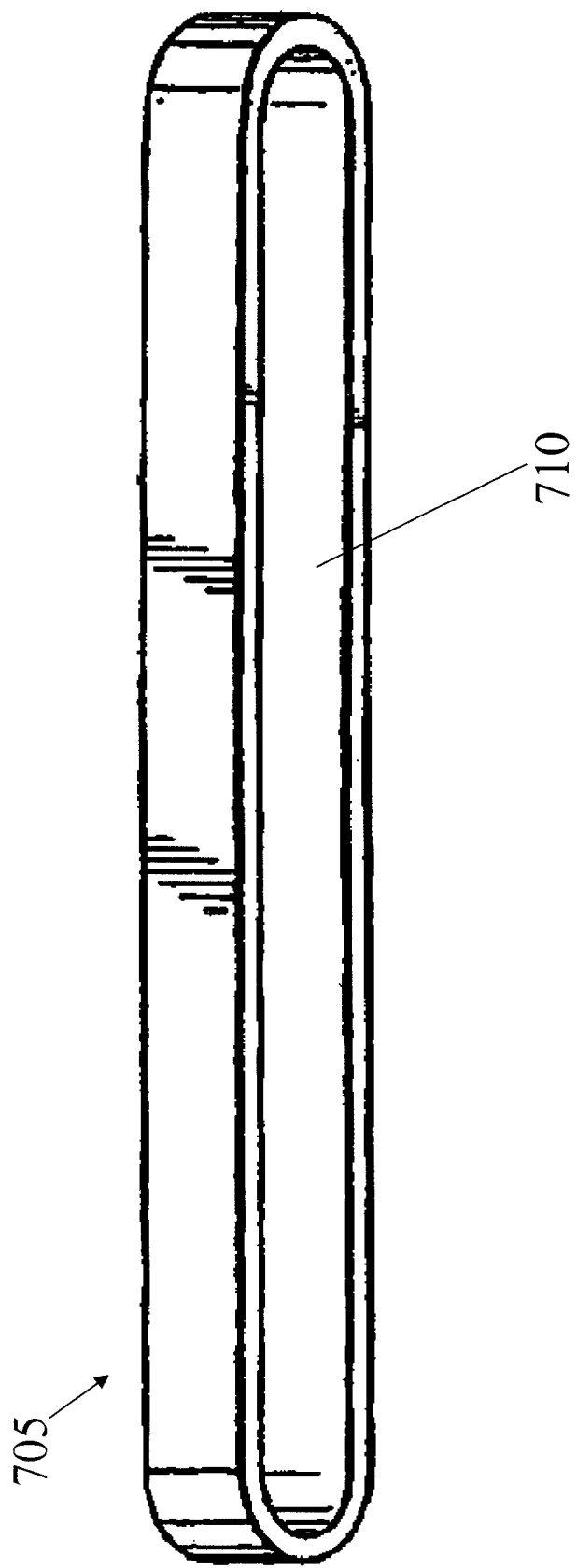
FIG. 10 shows an exemplary embodiment of a plate connector having an elongated slot for connecting to one or more bone screws.

In another embodiment, a loop or slotted plate connector is used in the cantilever framework in place of the rod. FIG. 10 shows an exemplary embodiment of a loop connector 705 having an elongated slot 710 for connecting to one or more bone screws. U.S. Pat. Nos. 6,083,224; 6,645,207; 6,682,530 and 6,884,241, which are incorporated herein by reference, demonstrate use of a slotted plate or similar loop connector member to inter-connect bone screws. When connected to a rigid screw, the slotted plate or similar loop connector 705 provides the cantilever framework needed for stability while permitting dynamic screw translation along its long axis within slot 710. Alternatively, the dynamic screw of FIG. 9 may be used, for example, to provide rotational motion while maintaining the upper portion of the assembly stationary relative to connector 705. In this way, the connector 705 effectively functions like the rod shown in FIGS. 1-3. It should be appreciated that the rigid and dynamic screw assemblies disclosed herein are illustrative and that the method itself may be used with any rigid and dynamic fasteners.

The preceding disclosure described devices and methods through which alignment may be corrected and motion may be preserved even in those degenerated segments that currently require fusion and complete immobilization. In the foregoing method, a rigid screw and rod are used as a rigid cantilever framework onto which other vertebral segments may be attached using dynamic bone screw assemblies. Depending on the anchor site, the dynamic connectors may be attached on one side of the rigid cantilever framework or on both sides of it. In the cervical spine, for example, stability can be provided to a large segment of the neck by placement of a rigid bone screw in an intermediate level (usually C5) and then rigidly connecting it to a rod. This forms a cantilever framework onto which dynamic anchors can be attached. The dynamic screws are attached to an upper level (usually C2) and a lower level (usually C7 or T1) and, collectively, the construct provides effective stabilization the neck while preserving motion.

Any of the screw assemblies, inter-connectors and/or their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, the outer surface of the bone screw assemblies may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the screw assemblies, inter-connectors and/or any component can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method to stabilize the movement of vertebral bones of a subject, comprising:

identifying vertebral bone levels to be stabilized, wherein at least one vertebral bone exhibits undesirable movement in at least one plane;

identifying a stable vertebral bone level and rigidly affixing at least a first bone fastener onto the stable vertebral bone level;

attaching a first segment of an interconnecting member onto a receiving portion of the first bone fastener, wherein the first bone fastener includes a deployable locking mechanism that reversibly advances from a first position to a second position, wherein the first segment of the interconnecting member is movable relative to the receiving portion of the first bone fastener when the locking mechanism is in the first position and wherein the first segment of the interconnecting member is rigidly affixed to the receiving portion of the first bone fastener when the locking mechanism is fully advanced to the second position;

extending the interconnecting member outward from the first bone fastener so as to form a cantilever construct, wherein the interconnecting member is rigidly immobilized within at least one predetermined plane;

affixing a second segment of the interconnecting member to an interconnecting member receiving portion of a second bone fastener;

attaching at least the second bone fastener onto a vertebral bone to be stabilized, wherein the second bone fastener includes at least a bone engagement member, an interconnecting member receiving portion and a deployable locking mechanism that reversibly advances from a first position to a second position, wherein the second segment of the interconnecting member is movable relative to the receiving portion of the second bone fastener when the locking mechanism is in the first position and wherein the second segment of the interconnecting member is rigidly affixed to the receiving portion of the second bone fastener when the locking mechanism is fully advanced to the second position, and wherein the bone engagement member remains movable relative to the interconnecting member when the locking mechanism is in any position;

fully advancing the locking mechanism of the first bone fastener to the second position;

fully advancing the locking mechanism of the second bone fastener to the second position.

2. A method as in claim 1, wherein the bone engagement member of the second bone fastener is rotationally movable relative to the interconnecting member when the locking mechanism of the second bone fastener is in any position.

3. A method as in claim 1, wherein movement between the bone engagement member of the second bone fastener and a remainder of the second bone fastener is biased towards a first, equilibrium position by a resilient member of the second bone fastener and wherein the resilient member functions to urge a return of the bone engagement member and the remainder of the second bone fastener towards the equilibrium position after a load acting upon the bone engagement member has been removed.

4. A method as in claim 1, wherein the second segment of the interconnecting member that is attached onto the receiving portion of the second bone fastener is movable relative to a separate segment of the interconnecting member.

5. A method as in claim 4, wherein movement between the second segment of the interconnecting member that is attached to the receiving portion of the second bone fastener and the separate segment of the interconnecting member is biased towards a first, equilibrium position by a resilient member and wherein the resilient member urges a return of the second segment of the interconnecting member that is attached to the receiving segment of the second bone fastener and the separate segment of the interconnecting member towards the equilibrium orientation after a load acting upon the second bone fastener has been removed.

6. A method as in claim 1, wherein the interconnecting member is rigidly immobilized in at least one plane and wherein that plane is parallel to a plane of undesirable movement of the vertebral bone to be stabilized.

7. A method as in claim 1, wherein the interconnecting member rigidly extends from the first bone fastener along the direction of a long axis of the spinal column.

8. A method as in claim 7, wherein the interconnecting member resists movement of an attached second bone fastener within a plane that is perpendicular to the long axis of the spinal column.

9. A method as in claim 1, wherein a vertical distance between a bone engagement member of the first bone fastener and the bone engagement of the second fastener along the direction of the long axis of the spine is permitted to vary after the locking member of each of the first and second bone fastener has been fully advanced to the second position.

10. A method as in claim 1, wherein at least one vertebral bone to be stabilized also exhibits mal-alignment in at least one plane relative to a adjacent bones.

11. A method to stabilize the movement of vertebral bones of a subject, comprising:
identifying vertebral bone levels to be stabilized, wherein at least one vertebral bone exhibits undesirable movement in at least one plane;
identifying a stable vertebral level and rigidly affixing at least a first bone fastener onto the stable vertebral level;
attaching a first segment of an interconnecting member onto a receiving portion of the first bone fastener, wherein the first bone fastener includes a bone engagement member, an interconnecting member receiving portion and a deployable locking mechanism that reversibly advances from a first position to a second position, wherein the attached first segment of the interconnecting member is movable relative to the receiving portion of the first bone fastener when the locking mechanism is in the first position and, wherein the attached first segment of the interconnecting member is rigidly affixed to the receiving portion of the first bone fastener when the locking mechanism is fully advanced to the second position;
extending the interconnecting member outward from the first bone fastener so as to form a cantilever construct, wherein the interconnecting member is rigidly immobilized in at least one plane;
affixing a second segment of the interconnecting member to an interconnecting member receiving portion of a second bone fastener;
attaching the second bone fastener onto a vertebral bone to be stabilized, wherein the second bone fastener includes a bone engagement member, an interconnecting member receiving portion, and a deployable locking mechanism that, when deployed, maintains the bone engagement member and the interconnecting member in proximity, and wherein the bone engagement member remains movable relative to the interconnecting member, and wherein movement between the bone engagement member and the interconnecting member receiving portion of the second bone fastener is biased towards a first, equilibrium position by a resilient member, and wherein the resilient member acts to urge a return of the bone engagement member and the interconnecting member receiving portion of the second fastener towards the equilibrium orientation after a load acting upon the bone engagement member has been removed;
fully advancing the locking mechanism of the first bone fastener to the second position;
deploying the locking mechanism of the second bone fastener so as to maintain the bone engagement member and the interconnecting member in proximity.

12. A method as in claim 11, wherein the bone engagement member of the second bone fastener is rotationally movable relative to the interconnecting member when the locking mechanism of the second fastener is in any position.

13. A method as in claims 11, wherein the second segment of the interconnecting member that is attached to the interconnecting member receiving portion of the second bone fastener is movable relative to an additional segment of the interconnecting segment.

14. A method as in claims 11, wherein movement between the second segment of the interconnecting member that is attached to the receiving portion of the second fastener and the first segment of the interconnection member are biased towards a first, equilibrium position by a resilient member and wherein the resilient member functions to urge a return of the second segment of the interconnecting member and the first segment of the interconnecting member towards the equilibrium orientation after a load acting upon the second fastener has been removed.

15. A method as in claim 11, wherein the interconnecting member is rigidly immobilized in at least one plane and wherein that plane is parallel to the plane of vertebral mal-alignment of the vertebral bone to be stabilized.

16. A method as in claim 11, wherein the interconnecting member rigidly extends from the first bone fastener along a direction of the long axis of the spinal column.

17. A method as in claim 11, wherein the interconnecting member resists movement of an attached second fastener within a plane that is perpendicular to a long axis of the spinal column.

18. A method as in claim 11, wherein a vertical distance between the bone engagement member of the first bone fastener and the bone engagement member of the second bone fastener along a direction of the long axis of the spine may vary after the locking member of each of the first and second fasteners has been fully advanced to the second position.

* * * * *